United States Patent [19]

Gale et al.

[11] 3,960,667

[45] June 1, 1976

[54] ANTIBIOTIC A23187 AND PROCESS FOR PREPARATION THEREOF

[75] Inventors: Richard M. Gale; Calvin E. Higgens; Marvin M. Hoehn, all of Indianapolis, Ind.

[73] Assignee: Eli Lilly and Company, Indianapolis, Ind.

[22] Filed: July 8, 1975

[21] Appl. No.: 594,157

Related U.S. Application Data

[60] Continuation-in-part of Ser. No. 237,532, March 23, 1972, abandoned, Division of Ser. No. 434,312, Jan. 17, 1974.

[52] U.S. Cl. ............................................. 195/80 R
[51] Int. Cl.² .......................................... C12D 9/00
[58] Field of Search ................................... 195/80 R

[56] References Cited

UNITED STATES PATENTS 2,928,844   3/1960   Boer et al. ...................... 195/80 R

OTHER PUBLICATIONS

Merck Index, p. 228, 8th Edition, 1968.

*Primary Examiner*—A. Louis Monacell
*Assistant Examiner*—Robert J. Warden
*Attorney, Agent, or Firm*—William B. Scanlon; Everet F. Smith

[57] ABSTRACT

Antibiotic A23187 and process for production thereof by submerged aerobic culture of *Streptomyces chartreusis* NRRL 3882. The antibiotic demonstrates antimicrobial activity and exhibits ionophorous properties, with a specificity for divalent cations.

2 Claims, 2 Drawing Figures

ANTIBIOTIC A23187 AND PROCESS FOR PREPARATION THEREOF

CROSS-REFERENCE

This application is a continuation-in-part of copending application Ser. No. 237,532 filed Mar. 23, 1972 now abandoned. This is a division, of application Ser. No. 434,312 filed Jan. 17, 1974.

BACKGROUND OF THE INVENTION

Bacterial and fungal infections in humans can be the cause of serious and life-threatening diseases. Although antimicrobial agents have been discovered which are effective against these organisms, there remains a need for additional agents to combat the spread of these microorganisms.

SUMMARY

Antibiotic A23187 is produced by culturing *Streptomyces chartreusis* NRRL 3882 in a nutrient culture medium containing assimilable sources of carbon, nitrogen and inorganic salts under submerged aerobic fermentation conditions and is isolated in the form of its mixed calcium-magnesium salt from the mycelial growth by extraction with an organic solvent. The antibiotic is purified by chromatography and crystallization procedures.

The antibiotic A23187 is an acidic, nitrogen-containing substance which inhibits the growth of microorganisms pathogenic to animal and plant life and which displays ionophorous properties with a high specificity for divalent cations.

Detailed Description

This invention relates to a novel antibiotic and its preparation. More particularly, this invention relates to an acidic, nitrogen-containing antibiotic, designated herein as A23187 and to the metal salts thereof.

The structure of antibiotic A-23187 is represented by the following formula:

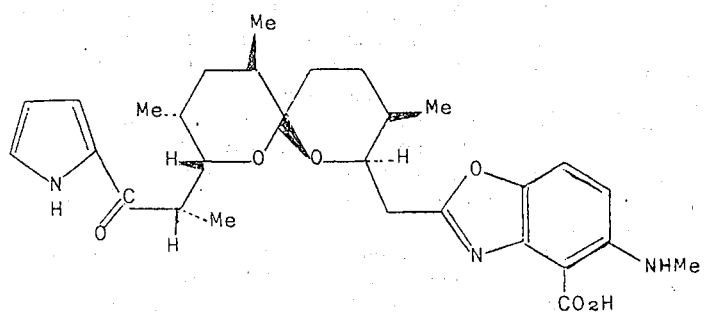

As shown, the antibiotic is a monocarboxylic acid containing an α-ketopyrrole and a benzoxazole moiety. The structure of A-23187 was determined by analysis of its nuclear magnetic resonance spectrum (nmr), mass spectroscopy and X-ray analysis and is in agreement with the physical data presented in the following paragraphs.

In the above formula the dotted bonding lines indicate that the bonded group is partially located below the plane of the ring to which it is attached. The spikes indicate that the attached group is positioned above the plane of the ring.

The antibiotic A-23187 is conveniently recovered from the fermentation medium in which it is produced in the form of the mixed calcium-magnesium salt of the antibiotic. The mixed salt and the free acid form of the antibiotic are characterized by the data presented in the following paragraphs.

The mixed calcium-magnesium salt of A23187 is a colorless crystalline solid, with a melting point of 230°–250°C. (decomp.). It is insoluble in water, very slightly soluble in the lower alcohols such as methanol, ethanol, isopropanol and the like, very soluble in the lower alkyl chlorinated hydrocarbons such as, methylene chloride, chloroform, dichloroethane and the like, the lower alkyl ketones such as acetone, methylethyl ketone, diethyl ketone and the like, esters formed with the lower alkyl carboxylic acids and lower alcohols such as methyl acetate, ethyl acetate, methyl propionate, amyl acetate, methyl butyrate and the like, and insoluble in hydrocarbons such as pentane, hexane, heptane and the like. Because of its crystalline nature and ease of preparation, it is conveniently employed for characterization purposes, although the free acidic form can also be so utilized, as will appear hereinafter.

Electrometric titration of the mixed calcium-magnesium salt A23187 in 90 percent dimethylsulfoxide indicates the presence of one group with a pKa' value of 6.9. The molecular weight, calculated from titration data, is approximately 550. A23187 is optically active, having a specific rotation, $[\alpha]_D^{25}$, of + 396°, at a concentration of 1% in chloroform.

Figure 1:
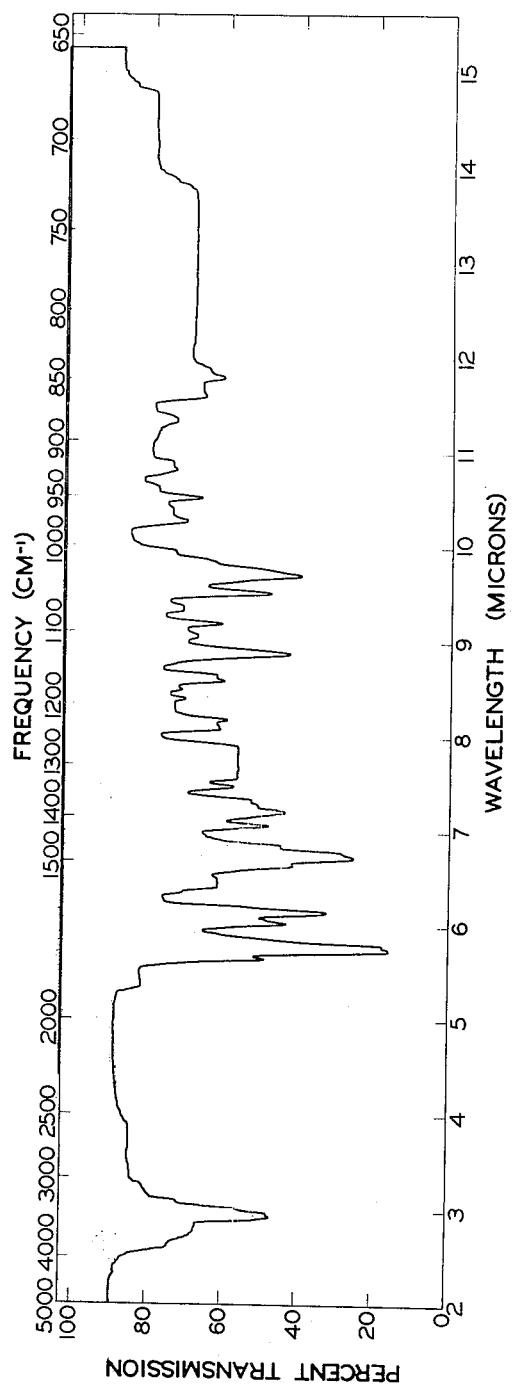

Elemental analysis shows A23187 calcium-magnesium salt to have approximately the following composition:

63.43 percent carbon
6.49 percent hydrogen
7.40 percent nitrogen
17.20 percent oxygen
1.68 percent magnesium
0.61 percent calcium The infrared absorption spectrum of A23187 as the mixed calcium-magnesium salt in chloroform solution is shown in FIG. 1 of the accompanying drawings. The following distinguishable maxima in the spectrum are observable over the range of 2.0 to 15.0 microns.

| | |
|---|---|
| 3.07–3.30 (broad) | 8.94 (W) |
| 3.41 (M) | 9.05 (W–M) |
| 6.12 (W) | 9.10 (W–M) |
| 6.21 (S) | 9.34 (M) |
| 6.26 (S) | 9.52 (W) |
| 6.50 (M) | 9.65 (W) |
| 6.61 (M) | 9.80 (W) |
| 6.90 (W) | 9.99 (M) |
| 7.10 (W) | 10.16 (M) |
| 7.19 (M–S) | 10.30 (W) |
| 7.30 (W) | 10.42 (W) |
| 7.52 (W–M) | 10.72 (W) |

-continued

| | |
|---|---|
| 7.67 (W—M) | 10.85 (W) |
| 7.73 (W) | 10.99 (W) |
| 7.80 (W) | 11.10 (W) |
| 7.94 (W) | 11.29 (W) |
| 8.55 (W) | 11.80 (W) |
| 8.64 (W) | 12.05 (W) |
| 8.86 (W) | 12.25 (W) |

Band intensities are indicated as S(strong), M(medium), and W(weak).

The ultraviolet absorption spectrum of the mixed calcium-magnesium salt of A23187 in ethanol shows several maxima, as outlined in Table I.

TABLE I

Ultraviolet absorption spectra of the calcium-magnesium salt of A23187
$E_{1cm}^{1\%}$

| Absorption maxima (mμ) | Acid | Neutral | Basic |
|---|---|---|---|
| 202 | | 425 | |
| 204 | 435 | | |
| 226 | 405 | | |
| 228 | | 490 | |
| 262 (S) | | 152 | |
| 272 (S) | | 130 | |
| 278 | 290 | | |
| 285 (S) | 270 | | |
| 292 | | | 340 |
| 303 | | 278 | |
| 353 | | | 90 |
| 370 | | 109 | |
| 380 | 50 | | |

The acidic form of A23187 crystallizes from acetone as colorless needles melting at about 181°–182°C. Its solubility pattern is similar to that of the mixed calcium magnesium salt. A23187 is optically active, having a specific rotaton, $[\alpha]_D^{25}$, of + 362° at a concentration of 1% in chloroform. A 1% solution of A23187 in propanol exhibits an optical rotation, $[\alpha]_D^{25}$ + 378°.

Elemental analysis of A23187 indicates the following composition:

66.75 percent carbon
7.12 percent hydrogen
7.86 percent nitrogen
18.13 percent oxygen Mass spectral data indicate the molecular weight of A23187 to be 523. These data, combined with the elemental analysis, indicate that the empirical formula is $C_{29}H_{37}N_3O_6$.

Figure 2:
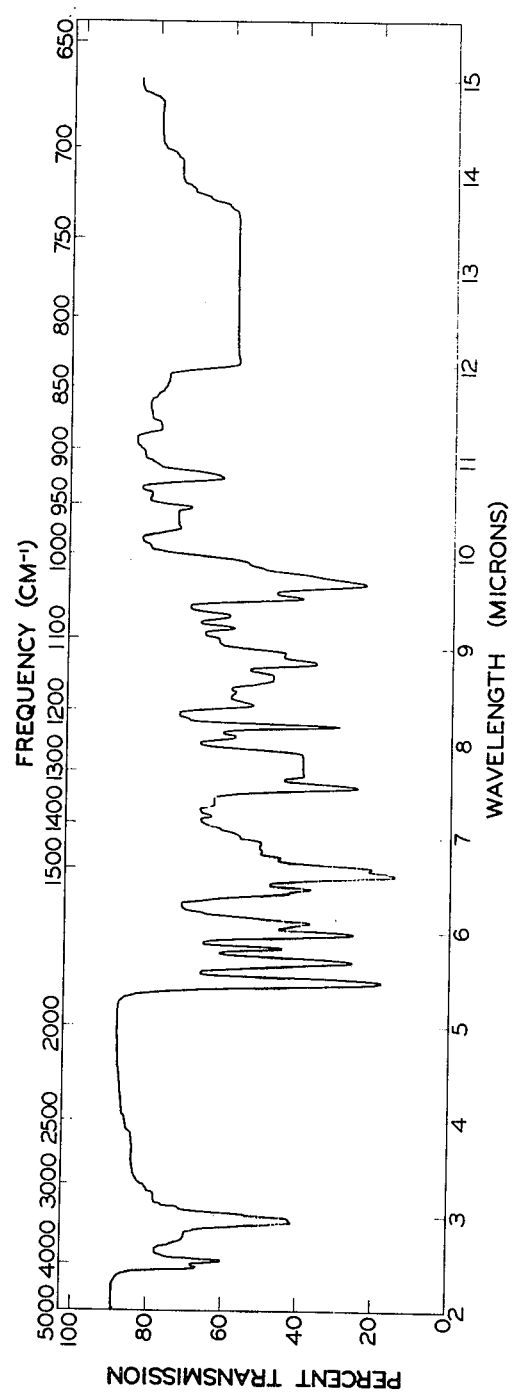

The infrared absorption spectrum of A23187 free acid is shown in FIG. 2 of the accompanying drawings. The following distinguishable maxima in the spectrum are observed over the range of 2.0 to 15.0 microns:

| | |
|---|---|
| 2.94 (W) | 8.54 (W) |
| 3.02 (W—M) | 8.65 (M) |
| 3.41 (M) | 8.87 (W) |
| 5.94 (S) | 9.00 (W) |
| 6.16 (M—S) | 9.15 (W) |
| 6.30 (M) | 9.31 (M) |
| 6.45 (M—S) | 9.42 (W) |
| 6.56 (M) | 9.69 (W) |
| 6.93 (M) | 9.82 (W) |
| 7.07 (S) | 10.01 (M) |
| 7.15 (M—S) | 10.17 (S) |
| 7.27 (W) | 10.40 (M) |
| 7.32 (W) | 10.75 (W) |
| 7.42 (W) | 10.98 (W) |
| 7.70 (W) | 11.30 (W) |
| 8.00 (M) | 11.80 (W) |

A powder X-ray diffraction pattern of the crystalline manganese salt of A23187 using vanadium filtered chromium radiation and a wave length value of 2.2895A for calculating interplanar spacings gives the following values:

| d | $I/I_1$ |
|---|---|
| 13.0 | .60 |
| 11.95 | .60 |
| 10.20 | 1.00 |
| 8.20 | .50 |
| 7.10 | .30 |
| 6.50 | .20 |
| 5.98 | .02 |
| 5.53 | .30 |
| 5.20 | .30 |
| 4.90 | .20 |
| 4.68 | .05 |
| 4.50 | .40 |
| 4.28 | .10 |
| 4.24 | .10 |
| 4.09 | .35 |
| 3.95 | .35 |
| 3.72 | .05 |
| 3.69 | .05 |
| 3.50 | .02 |
| 3.30 | .15 |
| 3.09 | .10 |

X-ray analysis of a single crystal of the manganese salt of A23187 indicates that the space group is $2_1 2_1 2_1$ with four molecules in a unit cell having the dimensions:

$a = 19.39$ A
$b = 14.16$ A
$c = 27.59$ A

In addition to the mixed calcium magnesium salt of A23187, it is possible to prepare salts with other divalent cations such as manganese, cadmium, barium and the like. The monovalent cation salts of A23187, such as sodium, potassium and like salts can also be prepared by conventional chemical methods, for example by reacting the acidic form of the antibiotic with a base such as sodium hydroxide, potassium hydroxide, sodium carbonate, sodium bicarbonate, potassium carbonate, lithium hydroxide and like bases. As in the case of the mixed calcium magnesium salt certain salts such as the manganese and cadmium salts can be used in the isolaton of the antibiotic. Other salts of the antibiotic, such as the sodium and potassium salts can be used as pharmaceutically acceptable non-toxic cationic salts in pharmaceutical preparations.

Because of the acidic function present in antibiotic A23187, it is possible to prepare esters of this compound by methods known in the art. The mono methyl ester is conveniently prepared by the use of diazomethane.

The paper chromatographic behavior of the mixed calcium-magnesium salt of A23187 is shown by the $R_f$ values in Table II below. The values were obtained in the indicated solvent systems using Whatman number one paper. The location of the antibiotic on the chromatogram was determined by bioautograph using *Bacillus subtilis* as the detecting organism.

TABLE II

| Paper Chromatography of A23187 | |
|---|---|
| Solvent System | $R_f$ Value* |
| Methanol:0.1 N HCl (3:1) | 0.67 |
| Propanol, pyridine, acetic acid and water in the ratios of 15:10:3:12 | 0.91 |
| Methanol:0.05M sodium citrate at pH 5.7 (7:3). Paper buffered with 0.05M sodium citrate solution at pH 5.7. | 0.69 |
| Methanol, propanol and water in the ratios of 6:2:1. Paper buffered with potassium dihydrogen phosphate solution (.75M) at | |

TABLE II-continued

Paper Chromatography of A23187

| Solvent System | $R_f$ Value* |
|---|---|
| pH 4.0 | 0.77 |

*$R_f$ value is defined as the ratio of the distance traveled by the antibiotic from the origin to the distance traveled by the solvent front from the origin.

Thin layer chromatography on silica gel plates with ultraviolet light as a detecting agent can be used to identify A23187 and the mono methyl ester of A23187. The chromatographic behavior is shown in Table III below:

TABLE III

Chromatography of A23187 and A23187 methyl ester on silica gel plates

| Solvent System | $R_f$ Values A23187 | A23187 | methyl ester |
|---|---|---|---|
| Benzene:ethyl acetate (4:1) | 0.74 | (streaked back) | 0.22 |
| Benzene:ethyl acetate (2:1) | 0.89 | (streaked back) | 0.37 |
| Benzene:ethyl acetate (1:1) | 0.98 | (streaked back) | 0.63 |
| Benzene:ethyl acetate (1:3) | 0.93 | (streaked back) | 0.74 |

The novel antibiotic of this invention has an inhibitory action against the growth of microbial organisms, both bacteria and fungi, which are pathogenic to animal and plant life and is therefore useful in suppressing the growth of such organisms. The antibiotic A23187 is useful in wash solutions for sanitation purposes, as in the cleaning of equipment, floors or furnishings of contaminated rooms or laboratories. For such purposes, the antibiotic, or a salt thereof, is conveniently formulated as a solution in one of the lower chlorinated hydrocarbons, as for example, chloroform. Because it is relatively insoluble in water, the antibiotic is preferably employed as an emulsified formulation if it is desired to use a water-based formulation. The preparation of such formulations is readily accomplished by methods known in the art. The antibiotic can be employed in a wide range of concentrations. Because of its relatively high activity, concentratons of 100 to 500 parts per million are generally adequate for most purposes. The minimum inhibitory concentration of A23187 for a number of illustrative organisms are listed in Table IV. The letters bd refer to broth dilution and the letters ad refer to agar dilution.

TABLE IV

Antibiotic activity of A23187

| Test organism | Minimum inhibitory concentration (mcg/ml) | |
|---|---|---|
| Staphylococcus aureus 3055 | .78 | (bd) |
| Staphylococcus aureus 1130 | .048 | (bd) |
| Bacillus subtilis | .2 | (ad) |
| Streptococcus faecalis 80 | .097 | (bd) |
| Lactobacillus casei | .78 | (ad) |
| Leuconostoc citrovorum | .2 | (ad) |
| Mycobacterium avium | .4 | (ad) |
| Pasteurella hemolytica | 12.5 | (bd) |
| Pasteurella multocida | 0.39 | (bd) |
| Erysipelas insidiosa | <.048 | (bd) |
| Mycoplasma gallisepticum | 1.56 | (bd) |
| Saccharomyces pastorianus | 1.56 | (ad) |
| Candida albicans | 25 | (ad) |
| Trichophyton mentagrophytes | .78 | (ad) |
| Botrytis cinerea | 1.56 | (ad) |
| Ceratostomella ulmi | 6.25 | (ad) |
| Colletotrichum pisi | 6.25 | (ad) |
| Glomerella cingulata | 100 | (ad) |
| Helminthosporium sativum | 25 | (ad) |
| Penicillium expansum | 6.25 | (ad) |
| Pullularia sp. | 1.56 | (ad) |
| Cladosporium resinae | 6.25 | (ad) |

The acute toxicity of antibiotic A23187 in mice, expressed as $LD_{50}$, is about 10 mg/kg of body weight when the antibiotic is administered intraperitoneally.

Another characteristic feature of A23187 is its ability to form complexes with certain divalent cations. In experiments to determine the affinity of A23187 for such cations, the following order of reactivity is seen:

$$Mn^{++} \gg Ca^{++} = Mg^{++} > Sr^{++} > Ba^{++}$$

A23187 has appreciable affinity for $Cd^{++}$, moderate affinity for $Ni^{++}$, $Zn^{++}$, $Co^{++}$ and $Be^{++}$, and no apparent affinity for $Hg^{++}$. Because of its preferential binding of certain cations, A23187 can be employed in applications wherein the selective removal of particular cations is desired. Thus, for example, the antibiotic can be employed for the removal of certain toxic cations, such as cadmium, from industrial waste streams before such streams are discharged to the environment. In addition, A23187 could be employed as one component of an ion-specific electrode. Antibiotic A23187 can also be utilized as a component of a water conditioning device for the removal of divalent cations, especially calcium and magnesium.

The actinomycete used for the production of the antibiotic of this invention has been identified as a strain of *Streptomyces chartreusis* Calhoun and Johnson. The organism has been deposited with the permanent culture collection of the Northern Utilization Research and Development Division, Agricultural Research Service, United States Department of Agriculture, Peoria, Illinois. Its accession number in this collection is NRRL 3882. The strain was isolated from a soil sample collected in India by suspending portions of the sample in sterile deionized water and streaking the suspensions on nutrient agar in petri plates. After incubation at 25° – 35°C. until growth was attained, colonies of the A23187-producing organisms were transferred to agar slants with a sterile platinum loop. The agar slants were then incubated to provide a suitable inoculum for the production of A23187.

The methods employed in the taxonomic studies of the A23187-producing strain of *Streptomyces chartreusis*, NRRL 3882, were those recommended for the International Streptomyces Project [Shirling and Gottlieb, *Intern. Bull. Systematic Bacteriol.*, 16.313–340 (1966)]. Results of the taxonomic studies are summarized in the paragraphs which follow. Color names were assigned according to the Inter-Society Color Council-National Bureau of Standards (ISCC-NBS) method (Kelly and Judd, *The ISCC-NBS Method of Designating Colors and a Dictionary of Color Names*, U.S. Dept. of Commerce Circ. 553, Washington, D.C., 1955). Letters in parentheses refer to color blocks and underlined letters and numbers to color tabs in the Tresner and Backus color series [*Appl. Microbiol.*, 11:335–338 (1963)]. The Maerz and Paul color block designations

[*Dictionary of Color*, McGraw-Hill Book Co., Inc., New York, (1950)] are enclosed in brackets. ISP numbers refer to International Streptomyces Project media (available from Difco Laboratories, Detroit, Michigan). Observations were made following incubation at 30°C. for fourteen days unless otherwise noted.

The principal morphological characteristics of the A23187-producing strain of *Streptomyces chartreusis* used in this invention are as follows: Sporophores are spiral, ranging from simple one or two spiral sporophores to short, compact spirals, and bear oval to spherical spores $1.05\mu \times 1.08\mu$ in size. Spores are characteristically spiny as observed by electron microscopy and occur in chains of from 10 to 50. Aerial mycelium and spores are pale-blue to greenish blue "en masse."

Substrate mycelium is from light yellow to light yellow brown to grayish greenish olive. A brown soluble pigment is produced when the organism is grown on two media.

The organism which produces the antibiotic of this invention is assigned to the Spiral-Blue series of Pridham et al [*Appl. Microbiol.*, 6:52–79 (1958)] and to the Blue series of Tresner and Backus [*Appl. Microbiol.*, 11:335–338 (1963)].

*Microscopic Morphology, Cultural Characteristics and Physiology of Streptomyces chartreusis NRRL 3882*

| | |
|---|---|
| Microscopic Morphology: | Sporophores are spiral and range from simple one or two coiled spirals to short, compact spirals. Spores are oval to spherical, $1.05\mu \times 1.08\mu$, and born in chains of from 10 to 50 spores. Spores are spiny as determined by electron microscopy. |
| Cultural characteristics: | |
| ISP Medium No. 2 | Abundant growth; reverse medium brown [11J4]. Abundant aerial mycelium and spores, pale blue (B) 19dc [34B2]. No soluble pigment. |
| ISP Medium No. 3 | Abundant growth; reverse grayish blue [35B1]. Abundant aerial mycelium and spores, pale blue (B) 19dc [36B2]. No soluble pigment. |
| ISP Medium No. 4 | Abundant growth; reverse pale yellow [11C2]. Abundant reverse pale mycelium and spores, pale blue (B) 19dc [34C2]. Brown soluble pigment. |
| ISP Medium No. 5 | Abundant growth; reverse pale yellow green [10C1]. Abundant aerial mycelium and spores, pale blue (B) 19dc 33B1]. No soluble pigment. |
| Czapek's Medium | Abundant growth; reverse light yellow brown. No aerial mycelium or spores. Brown soluble pigment. |
| Tryptone Yeast | Scant growth. No color assignment made. |
| Emerson's Agar | Abundant growth; reverse light yellow [11I2]. No aerial mycelium or spores. No soluble pigment. |
| Tomato Paste-Oatmeal Agar | Abundant growth; reverse light yellow [11I2]. Abundant aerial mycelium and spores, light greenish blue (B) 18ec [36B2]. No soluble pigment. |
| Glucose Asparagine Agar | Abundant growth; reverse pale yellow green [19B2]. Abundant aerial mycelium and spores, pale blue (B) 19dc [33D2]. No soluble pigment. |
| Tyrosine Agar | Scant growth; reverse pale yellow green to grayish ivory [10B1] to [10B2]. Scant aerial mycelium and spores, with (W)a [10A1]. No soluble pigment. |
| Nutrient Agar | Fair growth; reverse light grayish olive [13B2]. No aerial mycelium or spores; no color assignment made. No soluble pigment. |
| Bennett's Agar | Abundant growth; reverse grayish greenish olive [12E2]. Abundant aerial mycelium and spores, pale blue (B) 19dc [34E3]. No soluble pigment. |
| Calcium Malate | Abundant growth; reverse pale yellow green [10B1]. Abundant aerial mycelium and spores, pale blue (B) 19dc [ 34B2]. Brownish green soluble pigment. |
| Glycerol-Glycine | Abundant growth; reverse light yellow [11I2]. Abundant aerial mycellium and spores, purplish white (W) 13ba [34B2]. No soluble pigment. |
| Physiology: | |
| Nitrate Reduction | Positive |
| Skim milk | Heavy ring of growth. No curd or clearing. Slight sediment. |
| Temperature requirements | Fair growth at 26°C. Abundant growth and sporulation at 30°–43°C. with slightly less sporulation at 43°C. No growth at 49°C. |
| Gelation liquiefaction | Negative after 14 days |

Table V summarizes the results of the carbon utilization tests carried out on the A23187-producing strain of *Streptomyces chartreusis*, NRRL 3882. Symbols employed in the table are as follows:

+ = positive utilization
(−) = questionable utilization
− = no utilization

TABLE V

Carbon Utilization of S. Chartreusis, NRRL 3882

| Substrate | Response |
|---|---|
| Rhamnose | + |
| Arabinose | + |
| Cellulose | (−) |
| Xylose | + |
| Cellobiose | + |
| Inositol | + |
| Sucrose | + |
| Glucose | + |
| Fructose | + |
| Raffinose | + |
| Mannitol | + |

The culture medium employable in producing antibiotic A23187 by cultivation of the above described organism can be any one of several media, since, as is apparent from the above-described utilization tests, the organism is capable of utilizing different energy sources. However, for economy of production, maximum yield of antibiotic, and ease of isolation of the antibiotic, certain culture media containing relatively simple nutrient sources are preferred. Thus, for example, glucose is one of the preferred sources of carbohydrate, although fructose, sucrose, mannitol, dextrin, starch and the like can also be employed. Preferred sources of nitrogen include beef extract, casein, soybean meal and the like.

Nutrient inorganic salts to be incorporated in the culture media can include the customary salts capable of yielding sodium, potassium, ammonium, calcium, phosphate, chloride, sulfate and like ions. Additionally, sources of growth factors such as distillers' solubles and yeast extracts can be included with enhanced results.

As is necessary for the growth and development of other microorganisms, essential trace elements should also be included in the culture medium for growing the actinomycete employed in this invention. Such trace elements are commonly supplied as impurities incidental to the addition of other constituents to the media.

The initial pH of the culture medium can be varied widely. However, it has been found desirable that the initial pH of the medium be between about 6.0 and about 7.5. As has been observed with other actinomycetes, the pH of the medium gradually increases throughout the growth period of the organism while antibiotic A23187 is being produced, and may attain a level from about 6.5 to about 8.0, the final pH being dependent at least in part on the initial pH of the medium, the buffers present in the medium, and the period of time the organism is permitted to grow.

Submerged, aerobic cultural conditions are the conditions of choice for the production of antibiotic A23187. For the production of relatively small amounts, shake flasks can be employed; but for the preparation of large amounts, submerged aerobic culture in sterile tanks is preferred. The medium in the sterile tank can be inoculated with a sporulated suspension; but because of the growth lag experienced when a sporulated suspension is used as the inoculum, the vegetative form of the culture is preferred. By thus avoiding the growth lag, more efficient use of the fermentation equipment is realized. Accordingly, it is desirable first to produce a vegetative inoculum of the organism by inoculating a relatively small quantity of culture medium with the spore form of the organism, and when a young, active vegetative inoculum has been obtained, to transfer the vegetative inoculum aseptically to the large tank. The medium in which the vegetative inoculum is produced can be either the same as or different from the medium utilized for the large-scale production of antibiotic A23187.

The organism grows best at temperatures in the range of about 26°C. to about 33°C. Optimal A23187 production appears to occur at temperatures of about 30°C.

As is customary in aerobic submerged culture processes, sterile air is blown through the culture medium. For efficient growth of the organism and antibiotic production, the volume of air in the tank production of antibiotic A23187 preferably is upwards of 0.1 volume of air per minute per volume of culture medium. Optimal growth and antibiotic production are obtained when the volume of air used is at least one-half volume of air per minute per volume of culture broth.

The rate of production of antibiotic A23187 and the concentration of the antibiotic activity in the culture medium can be followed readily during the growth period of the microorganism by testing samples of the culture medium for their antibiotic activity against organisms known to be susceptible to the antibiotic. A suitable assay method for antibiotic A23187 employs the plate assay with *Bacillus subtilis*. Any of the conventional bioassay techniques can be employed, however, such as the standard turbidimetric or cup-plate methods, as well as the paper disc assay upon agar plates.

In general, maximum production of the antibiotic occurs within about 2 to 5 days after inoculation of the culture medium when submerged aerobic culture or shake flask culture is employed.

Antibiotic A23187 can be recovered from the mycelium by the use of extractive techniques. In a preferred recovery process, the mycelium is separated from the fermentation beer by conventional means such as filtration with the use of a filter aid or by centrifugation. The mycelial mass is washed with water and then suspended in a water miscible solvent such as methanol. The methanol extract is evaporated to remove the methanol. Antibiotic A23187 can be recovered from the resulting aqueous solution by extraction at alkaline pH with a suitable solvent. Ethyl acetate is preferred. The ethyl acetate solution is concentrated to an oil, and the oil is dissolved in a suitable solvent such as methylene dichloride or chloroform. The addition of methanol to the methylene dichloride solution results in the precipitation of antibiotic A23187 mixed calcium-magnesium salt.

An additional quantity of antibiotic A23187 can be recovered from the mycelial mass by further extraction with methanol at elevated temperatures, for example, between 60° and 65°C. The methanol extracts are concentrated to about one-fourth the original volume, and antibiotic A23187 mixed calcium magnesium salt is precipitated. Purification of antibiotic A23187 calcium magnesium salt can be accomplished by chromatography of solutions of the antibiotic on columns packed with any suitable absorbent, such as silica gel, alumina, carbon, cellulose and the like. For example, impure preparations of the calcium magnesium salt of A-23187 can be purified by separating the antibiotic from other constituents produced during the fermentation by chromatography over a nonionic absorbent and preferably silica gel. Considerable purification can likewise be obtained by chromatography over an activated carbon absorbent. Accordingly a solution of the antibiotic mixed salt in a solvent such as methylene chloride or chloroform is poured into a column packed with such an absorbent, for example silica gel and the column washed with benzene. The antibiotic is then eluted from the absorbent with a suitable solvent or solvent mixture and desirably a mixture of benzene and ethyl acetate. Multiple fractions are collected and those fractions found by thin layer chromatography to contain the antibiotic are combined and evaporated to obtain the purified antibiotic mixed salt as an amorphous residue.

The antibiotic can be further purified by crystallization. Methanol is a desirable solvent for the crystallization of the mixed salt.

The purified antibiotic A23187 in the free acid form is best obtained by the acidification of the crystalline mixed calcium magnesium salt form of the antibiotic prepared as described above.

This invention is further illustrated by the following Examples, however, the methods and procedures described therein are not intended to be limiting of the invention.

EXAMPLE 1

A. Shake-flask fermentation of A23187

The A23187-producing culture is prepared and maintained on an agar slant having the following composition:

| | |
|---|---|
| Dextrin 700 (A.E. Staley Co., Decatur, Ill.) | 10.0 g |
| N-Z amine A (Sheffield) Chemical, a division of National Dairy Products Corp., Norwich New York) | 2.0 g |
| Beef extract | 1.0 g |
| Yeast extract | 1.0 g |
| Agar | 20.0 g |
| Deionized water | 1 liter |

The slant is inoculated with the A23187-producing culture, NRRL 3882, and incubated at 30° C. for 4-6 days. The sporulated slant is covered with a small amount of sterile deionized water and gently scraped to provide an aqueous spore suspension.

One milliliter of the resulting spore suspension is used to inoculate 100 ml of sterile vegetative medium having the following composition:

| | |
|---|---|
| Glucose | 15.0 g |
| Soybean meal | 15.0 g |
| Corn steep solids | 5.0 g |
| CaCO$_3$ | 2.0 g |
| NaCl | 5.0 g |
| Tap water | 1 liter |

The inoculated vegetative medium is incubated for 24-48 hours at 30° C. on a reciprocal shaker having a two-inch stroke at 108 strokes per minute or on a rotary shaker operating at 250 r.p.m. A five ml portion of the resulting culture is then employed to inoculate 100 ml of sterilized production medium contained in a 500 ml Erlenmeyer flask and having the following composition:

| | |
|---|---|
| Soybean meal | 15.0 g |
| Casein | 1.0 g |
| NaNO$_3$ | 3.0 g |
| Glucose syrup | 20.0 g |
| Tap water | 1 liter |

The inoculated medium is allowed to ferment for 48–72 hours at 25°–30° C. on either a rotary shaker operating at 250 r.p.m. or on a reciprocal shaker operating at 108 strokes per minute. The terminal pH is 6.5 to 8.0. B. Tank fermentation of A23187.

The A23187-producing culture (NRRL 3882) is prepared and maintained on an agar slant having the following composition:

| | |
|---|---|
| Tomato paste | 20.0 g |
| Oatmeal | 20.0 g |
| Agar | 20.0 g |
| Deionized water | 1 liter |

The pH of the medium is adjusted to 6.7 with sodium hydroxide solution; after sterilization, the pH of the medium is 6.4.

The slant is inoculated with the A23187-producing culture and incubated at 34° C. for 7 days. The sporulated slant is covered with a small amount of sterile deionized water and gently scraped to provide an aqueous spore suspension.

Each slant is used to inoculate four 250 ml flasks each containing 50 ml of sterile vegetative culture medium having the following composition:

| | |
|---|---|
| Glucose | 15.0 g |
| Starch, Soluble | 30.0 g |
| Soybean grits | 15.0 g |
| Corn steep liquor | 20.0 g |
| NaCl | 5.0 g |
| CaCO$_3$ | 2.0 g |
| Tap water | 1.1 liters |

The pH of the medium is adjusted to 6.5 with sodium hydroxide solution; after sterilization, the pH of the medium is 6.9.

The inoculated vegetative medium is incubated for 48 hours at 30°C. on a rotary shaker operating at 250 r.p.m. A ten ml portion of the resulting culture is then employed to inoculate 200 ml of sterilized second-stage growth medium contained in a liter flask and having the same composition as that described above.

The inoculated medium is allowed to ferment for 48 hours at 30°C on a rotary shaker operating at 250 r.p.m. A 200 ml portion of the culture is used to inoculate 25 liters of the following medium in a 40-liter fermentor:

| | Percent |
|---|---|
| Glucose | 2.5 |
| Soybean grits | 1.5 |
| Acid-hydrolyzed casein | 0.1 |
| CaCO$_3$ | 0.3 |
| Tap water | 25 liters |

The pH of the medium is 7.3 after sterilization.

The inoculated medium is aerated at a rate of one-half volume of air per volume of culture per minute and is stirred with conventional agitators at 400 r.p.m.

The fermentation is carried out at 30°C. for 3 days.

C. Isolation of Antibiotic A23187 mixed calcium-magnesium salt.

Fifty liters of whole fermentaiton vroth obtained from an A23187 fermentation as described above was filtered with the aid of a commercial filter aid. The filtrate was discarded. The filter cake was then washed with 13 liters of water, and the water wash was discarded. The mycelial cake was then suspended in 8.5 liters of methanol. The resulting suspension was stirred at room temperature for one-half hour and filtered. The extracted mycelial cake was extracted twice more, following the above procedure. The filtrates were combined. The extracted mycelial cake was suspended in 11 liters of methanol and stirred at 60° – 65° C. The suspension was filtered and the extraction was repeated. The filtrates from the hot methanol extraction were combined and concentrated to about 4 liters. When the concentrate was cooled, the mixed calcium-magnesium salt of A23187 crystallized. The crystals were recovered by filtration and dried.

An additional amount of A23187 was recovered from the methanol filtrates from the room temperature extractions. These filtrates were combined and evaporated to remove the methanol. The resulting water solution was adjusted to pH 10 with sodium hydroxide solution. This solution was extracted with one-half volume ethyl acetate. The aqueous phase was discarded. The ethyl acetate extract was concentrated to an oil. The resulting oil was dissolved in a small volume of methylene dichloride. Methanol was added to this solution until the A23187 began to crystallize. The solution was held at 5° C. overnight. The crystals of the mixed calcium-magnesium salt of A23187 were recovered by filtration and dried.

EXAMPLE 2

Purification of the mixed calcium-magnesium salt of A23187

Twenty grams of an impure preparation of the mixed calciummagnesium salt of A23187 was dissolved in 90 ml benzene. The resulting solution was applied to a 3 cm × 107 cm column packed with silica gel (Grade 62, Matheson Coleman and Bell, Cincinnati, Ohio) in benzene. The column was washed with 2500 ml benzene to remove impurities. The A23187 was then eluted with a solution of benzene:ethyl acetate (95:5). Fractions were collected and monitored by thin-layer chromatography. The fractions containing A23187 were combined. The resulting solution was concentrated to dryness in vacuo. The residue was dissolved in hot methanol. The solution was cooled, allowing crystals of the mixed calciummagnesium salt of A23187 to form. The crystals were recovered by filtration, washed with cold methanol and dried.

EXAMPLE 3

Preparation of the free acid form of A23187

Three grams of the mixed calcium magnesium salt obtained as described in Example 1 were dissolved in 60 ml of ethyl acetate. The resulting solution was shaken with 50 ml of 0.1N HCl in a separatory funnel. The aqueous phase was discarded. The ethyl acetate phase was shaken again with 50 ml of 0.1 N HCl. The aqueous phase was discarded. The ethyl acetate solution was concentrated to dryness yielding a white to light yellow amorphous preparation of the acid form of A23187. The amorphous solid was dissolved in warm acetone and the solution was cooled in an ice-bath to precipitate crystalline A-23187 free acid. The crystalline precipitate is filtered and air dried. Melting point 181°–182°C.

EXAMPLE 4

Preparation of the mono methyl ester of A23187

Two hundred milligrams of the acid form of A23187, prepared according to the procedure in Example 3, was dissolved in 70 ml ethyl acetate. To the resulting solution was added 5 ml of a 10% solution of diazomethane in ether. The resulting mixture was allowed to stand at room temperature for 1 hour. The reaction mixture was then concentrated in vacuo to dryness. The dried residue was an amorphous preparation of the mono methyl ester of A23187. Mass spectral data indicated a molecular weight of 537.

EXAMPLE 5

Preparation of the manganese salt of A23187

Fifty milligrams of the mixed calcium magnesium salt prepared according to the procedure in Example 1 was dissolved in 5 ml of ethyl acetate. To the resulting solution was added 5 ml ethanol and 5 ml of 0.1 M aqueous solution of manganous acetate. The solution was allowed to stand at approximately 5° C. until light yellow prismatic crystals formed. The crystals were recovered and dried, yielding the manganese salt of A23187. Melting point: 225°–235° C. (decomp.)

We claim:
1. The method for producing the antibiotic A-23187 of the formula

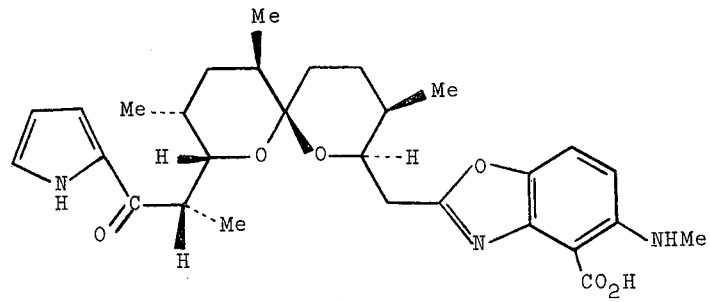

which comprises cultivating Streptomyces chartreusis NRRL 3882 in a culture medium containing assimilable sources of carbon, nitrogen and inorganic salts under submerged aerobic fermentation conditions until a substantial amount of antibiotic A-23187 is produced by said organism in said culture medium.

2. A method of producing the antibiotic of claim 1 which comprises cultivating *Streptomyces chartreusis* NRRL 3882 in a culture medium containing assimilable sources of carbon, nitrogen and inorganic salts under submerged aerobic conditions until a substantial amount of antibiotic A23187 is produced by said organism in said culture medium and recovering antibiotic A23187 from the mycelial growth.

* * * * *

UNITED STATES PATENT AND TRADEMARK OFFICE
CERTIFICATE OF CORRECTION

PATENT NO. : 3,960,667
DATED : June 1, 1976
INVENTOR(S) : Richard M. Gale, et al.

It is certified that error appears in the above-identified patent and that said Letters Patent are hereby corrected as shown below:

In column 3, line 37, "rotaton" should read -- rotation --.

In column 3, line 45, "Mass spectral data indicate the" should start a new paragraph.

In column 4, line 43, "isolaton" should read -- isolation --.

In column 8, line 27, delete "reverse pale" and substitute therefor -- aerial --.

In column 8, line 30, "33B1]" should read -- [33B1] --.

In column 12, line 5, "Tank fermentation of A23187." should be a separate paragraph.

In column 12, line 62, "vroth" should read -- broth --.

In column 13, lines 31 and 57, "calciummagnesium" should read -- calcium-magnesium --.

Signed and Sealed this

Twenty-eighth Day of September 1976

[SEAL]

Attest:

RUTH C. MASON
Attesting Officer

C. MARSHALL DANN
Commissioner of Patents and Trademarks